United States Patent [19]

Besecke et al.

[11] Patent Number: 5,354,895
[45] Date of Patent: Oct. 11, 1994

[54] OXADIMETHACRYLICS AND PREPARATION THEREOF

[75] Inventors: Siegmund Besecke, Hamelen; Andreas Deckers, Ludwigshafen; Harald Lauke, Mannheim, all of Fed. Rep. of Germany

[73] Assignee: BASF Aktiengesellschaft, Ludwigshafen, Fed. Rep. of Germany

[21] Appl. No.: 996,394

[22] Filed: Dec. 23, 1992

[30] Foreign Application Priority Data

Dec. 24, 1991 [DE] Fed. Rep. of Germany ....... 4142909

[51] Int. Cl.$^5$ .......................................... C07C 229/00
[52] U.S. Cl. .................................... 560/155; 560/181; 558/440; 558/462; 564/204; 564/207; 562/567; 562/595; 562/579
[58] Field of Search ................ 560/181, 155; 558/440, 558/462; 564/202, 207; 562/567, 579, 595

[56] References Cited

U.S. PATENT DOCUMENTS 4,889,948 12/1989 Mathies et al. ..................... 560/181

OTHER PUBLICATIONS

Mathies, L. et al. Polym. Commun. 29(10), 302–4 1988.
Polymer Preprints, American Chemical Society, Div. of Polymer Chemistry 31(1) 1990 503.
Coletti et al., *Macromolecules,* vol. 24, No. 8, 1991, pp. 2043–2047, "Mechanism Study of the Base-Catalyzed Ether . . . ".
*Chem. Abst. Service Reg. Handbook–Number Section 1989 Supplement,* 1989, The American Chemical Society.

*Primary Examiner*—Paul J. Killos

*Attorney, Agent, or Firm*—Keil & Weinkauf

[57] ABSTRACT

Oxadimethacrylics useful for preparing pollers have the general formula I $$CH_2=C(A)CH_2-O-CH_2C(B)=CH_2 \qquad I$$

where A and B are selected from the group consisting of $-COOR^1$, $-COR^1$, $-CONR^2R^3$ and $-CN$ with the proviso that $A \neq B$, and $R^1$, $R^2$ and $R^3$ are each defined as follows:

$R^1$ is hydrogen, $C_1$-$C_{18}$-alkyl, $C_3$-$C_8$-cycloalkyl, $C_3$-$C_8$-cycloalkyl-$C_1$-$C_5$-alkyl, wherein the cycloalkyl rings may be $C_1$-$C_4$-alkyl- or $C_1$-$C_4$-alkoxy-monosubstituted, -disubstituted or -trisubstituted, hydroxy-$C_1$-$C_5$-alkyl, amino-$C_1$-$C_5$-alkyl, N-$C_1$-$C_4$-alkylamino-$C_1$-$C_5$-alkyl, N,N-di-($C_1$-$C_4$-alkyl)amino-$C_1$-$C_5$-alkyl, $C_6$-$C_{18}$-aryl, $C_6$-$C_{18}$-aryl-$C_1$-$C_4$-alkyl, wherein the aryl groups may carry up to three of the following groups: halogen, $C_1$-$C_{22}$-alkyl, $C_1$-$C_4$-alkoxy, carboxyl, $C_1$-$C_4$-alkoxycarbonyl, aminocarbonyl, $C_1$-$C_4$-alkylaminocarbonyl, di($C_1$-$C_4$-alkyl)aminocarbonyl, nitrilo, nitro, amino, $C_1$-$C_4$-alkylamino, di($C_1$-$C_4$-alkyl)amino;

$R^2$ and $R^3$ are each hydrogen, $C_1$-$C_{18}$-alkyl, $C_3$-$C_8$-cycloalkyl, $C_3$-$C_8$-cycloalkyl-$C_1$-$C_5$-alkyl, wherein the cycloalkyl rings may be $C_1$-$C_4$-alkyl- or $C_1$-$C_4$-alkoxy-monosubstituted, -disubstituted or -trisubstituted, $C_8$-$C_{18}$-aryl, $C_8$-$C_{18}$-aryl-$C_1$-$C_4$-alkyl, wherein the aryl groups may carry up to three of the following groups: halogen, $C_1$-$C_{22}$-alkyl, $C_1$-$C_4$-alkoxy, carboxyl, $C_1$-$C_4$-alkoxycarbonyl, aminocarbonyl, $C_1$-$C_4$-alkylaminocarbonyl, di($C_1$-$C_4$-alkyl)aminocarbonyl, nitrilo, nitro, amino, $C_1$-$C_4$-alkylamino, di($C_1$-$C_4$-alkyl)amino.

4 Claims, No Drawings

OXADIMETHACRYLICS AND PREPARATION THEREOF

The present invention relates to oxadimethacrylics of the general formula I

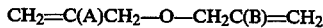

$$CH_2=C(A)CH_2-O-CH_2C(B)=CH_2 \quad \text{I}$$

where A and B are selected from the group consisting of $-COOR^1$, $-COR^1$, $-CONR^1R^3$ and $-CN$ with the proviso that $A \neq B$, and $R^1$, $R^2$ and $R^3$ are each defined as follows:

$R^1$ is hydrogen, $C_1$-$C_{18}$-alkyl, $C_3C_8$-cycloalkyl, $C_3C_8$-cycloalkyl-$C_1$-$C_5$-alkyl, wherein the cycloalkyl rings may be $C_1$-$C_4$-alkyl- or $C_1$-$C_4$-alkoxy-monosubstituted, -disubstituted or -trisubstituted, hydroxy-$C_1$-$C_5$-alkyl, amino-$C_1$-$C_5$-alkyl, N-$C_1$-$C_4$-alkylamino-$C_1$-$C_5$-alkyl, N,N-di-($C_1$-$C_4$-alkyl)amino-$C_1$-$C_5$-alkyl, $C_6$-$C_{18}$-aryl, $C_6$-$C_{18}$-aryl-$C_1$-$C_4$-alkyl, wherein the aryl groups may carry up to three of the following groups: halogen, $C_1$-$C_{22}$-alkyl, $C_1$-$C_4$-alkoxy, carboxyl, $C_1$-$C_4$-alkoxycarbonyl, aminocarbonyl, $C_1$-$C_4$-alkylaminocarbonyl, di($C_1$-$C_4$-alkyl)aminocarbonyl, nitrilo, nitro, amino, $C_1$-$C_4$-alkylamino, di($C_1$-$C_4$-alkyl)amino;

$R^2$ and $R^3$ are each hydrogen, $C_1$-$C_{18}$-alkyl, $C_3$-$C_{18}$-cycloalkyl, $C_3$-$C_8$-cycloalkyl-$C_1$-$C_5$-alkyl, wherein the cycloalkyl rings may be $C_1$-$C_4$-alkyl- or $C_1$-$C_4$-alkoxy-monosubstituted, -disubstituted or -trisubstituted, $C_6$-$C_{18}$-aryl, $C_6$-$C_{18}$-aryl-$C_1$-$C_4$-alkyl, wherein the aryl groups may carry up to three of the following groups: halogen, $C_1$-$C_{22}$-alkyl, $C_1$-$C_4$-alkoxy, carboxyl, $C_1$-$C_4$-alkoxycarbonyl, aminocarbonyl, $C_1$-$C_4$-alkylaminocarbonyl, di($C_1$-$C_4$-alkyl)aminocarbonyl, nitrilo, nitro, amino, $C_1$-$C_4$-alkylamino, di($C_1$-$C_4$-alkyl)amino.

The present invention further relates to processes for preparing the oxadimethyacrylics I and to the use of these compounds for preparing polymers.

Symmetrical oxadimethacrylics, i.e. those where $A=B$, are known. For instance, U.S. Pat. No. 4,889,948 and Polymer Preprints, American Chemical Society, Division of Polymer Chemistry 31(1) (1990) 503 disclose oxadimethacrylics of the general formula I'''

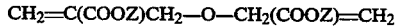

$$CH_2=C(COOZ)CH_2-O-CH_2(COOZ)=CH_2 \quad \text{I'''}$$

where Z is hydrogen, methyl, ethyl, n-butyl, isobutyl, tert-butyl, neopentyl, benzyl, phenethyl, trimethylcyclohexyl or tetrahydrofurfuryl.

Owing to their bifunctionality these compounds are widely used as monomeric building blocks, for example as monomers for preparing homopolymers, as comonomers and as crosslinkers. However, at present only a few, exclusively symmetrical oxadimethacrylics are available in adequate amounts. A further disadvantage is the usually inadequate purity of these compounds.

The oxadimethacrylics I''' can be obtained as described in U.S. Pat. No. 4,889,948 starting from alcohols of the type of alcohol III, $H_2C=C(A)CH_2OH$, but also starting from acrylics of type II, $H_2C=C(A)H$. The reaction of alcohols of type III to form the oxadimethacrylics I''' is carried out in this case by heating, but reaction over one to two days, besides resulting in appreciable polymerization of the monomers, gives only moderate yields of oxadimethacrylics I'''.

Reacting acrylics of type II with formaldehyde in the presence of the tertiary amine 1,4-diazabicyclo[2.2.2]octane (DABCO®) produces according to U.S. Pat. No. 4,889,948 mainly alcohols of type III, only minor amounts of the oxadimethacrylics I''', but higher (ether) homologs of the oxadimethacrylics I''' and polymeric by-products. Besides this lack of specificity, further disadvantages of the reaction are the long reaction times (from 10 to 20 days) and appreciable polymerization at above room temperature.

It is an object of the present invention to provide novel oxadimethacrylics in high purity.

We have found that this object is achieved by the oxadimethacrylics I defined at the beginning.

We have also found processes for preparing these compounds and a use thereof for preparing polymers.

The substituents $R^1$, $R^2$ and $R^3$ in the oxadimethacrylics I of the invention preferably have the following meanings:

$R^1$ hydrogen;

$C_1$-$C_{18}$-alkyl, preferably $C_1$-$C_{12}$-alkyl such as methyl, ethyl, n-propyl, isopropyl, n-butyl, sec-butyl, isobutyl, tert-butyl, n-pentyl, isopentyl, sec-pentyl, tert-pentyl, neopentyl, n-hexyl, n-heptyl, n-octyl, n-nonyl, n-decyl, n-undecyl, n-dodecyl and stearyl, particularly preferably $C_1$-$C_4$-alkyl such as methyl, ethyl, n-propyl, isopropyl, n-butyl, isobutyl, sec-butyl, tert-butyl;

$C_3$-$C_8$-cycloalkyl such as cyclopropyl, cyclopentyl, cyclohexyl, cycloheptyl, cyclooctyl, 4-methylcyclohexyl, 4-methoxycyclohexyl, 2,4,6-trimethylcyclohexyl;

$C_3$-$C_8$-cycloalkyl-$C_1$-$C_5$-alkyl such as cyclopropylmethyl, cyclopentylmethyl, cyclohexylmethyl, cyclopropylethyl, cyclopentylethyl, cyclohexylethyl, cyclopropylpropyl, cyclopentylpropyl, cyclohexylpropyl, cyclopentylbutyl, cyclohexylbutyl, cyclopentylpentyl, cyclohexylpentyl, cyclooctylpentyl;

hydroxy-$C_1$-$C_5$-alkyl such as hydroxymethyl, 2-hydroxyethyl, 2-hydroxypropyl, 3-hydroxypropyl, 4-hydroxybutyl, 5-hydroxypentyl, 2,2-dimethyl-3-hydroxypropyl;

amino-$C_1$-$C_5$-alkyl such as aminomethyl, 2-aminoethyl, 3-aminopropyl, 4-aminobutyl, 5-aminopentyl;

N-$C_1$-$C_4$-alkylamino-$C_1$-$C_5$-alkyl such as N-methylaminomethyl, 2-(N-methylamino)ethyl, 3-(N-methylamino)-propyl, 4-(N-methylamino)butyl, 5-(N-methylamino)-pentyl, N-ethylaminomethyl, N-n-propylaminomethyl, N-n-butylaminomethyl;

N,N-di($C_1$-$C_4$-alkyl)amino-$C_1$-$C_5$-alkyl such as N,N-dimethylaminomethyl, 2-(N,N-dimethylamino)ethyl, 3-(N,N-dimethylamino)propyl, 4-(N,N-dimethylamino)butyl, 5-(N,N-dimethylamino)pentyl, N,N-diethylaminomethyl, N,N-di(n-propyl)aminomethyl, N,N-di(isopropyl)aminomethyl, N,N-di(n-butyl)aminomethyl, N-ethyl-N-methyl-aminomethyl, N-methyl-N-propylaminomethyl;

$C_6$-$C_{18}$-aryl such as phenyl, naphthyl, anthracenyl, phenantrenyl, azulenyl, biphenylenyl, triphenylenyl, preferably phenyl, it being possible for the aryl radicals to carry up to three of the groups mentioned under $R^{11}$;

$C_6$-$C_{18}$-aryl-$C_1$-$C_4$-alkyl, preferably phenyl-$C_1$-$C_4$-alkyl such as benzyl, 2-phenylethyl, 3-phenylpropyl, 4-phenylbutyl, particularly preferably benzyl, 2-phenylethyl, 3-phenylpropyl, it being possible for the aryl groups to carry up to three of the groups mentioned under $R^{11}$;

$R^2$, $R^3$ $C_1$-$C_{18}$-alkyl such as mentioned for $R^1$, including particularly preferably $C_1$-$C_4$-alkyl such as methyl, ethyl, n-propyl, isopropyl, n-butyl, sec-butyl, isobutyl, tert-butyl;

$C_3$-$C_8$-cycloalkyl such as cyclopropyl, cyclopentyl, cyclohexyl, cycloheptyl, cyclooctyl, 4-methylcyclohexyl, 2,4,6-trimethylcyclohexyl;

$C_6$-$C_4$-aryl as mentioned for $R^1$, preferably phenyl, which may carry up to three of the groups mentioned under $R^{11}$;

$C_6$-$C_{18}$-aryl-$C_1$-$C_4$-alkyl such as mentioned for $R^1$, preferably phenyl-$C_1$-$C_4$-alkyl, particularly preferably benzyl, 2-phenylethyl, 3-phenylpropyl, wherein the phenyl group may carry up to three of the groups mentioned under $R^{11}$; and $R^{11}$ halogen such as fluorine, chlorine, bromine and iodine, $C_1$-$C_{22}$-alkyl such as methyl, ethyl, n-propyl, isopropyl, n-butyl, sec-butyl, isobutyl, tert-butyl, n-pentyl, isopentyl, sec-pentyl, tert-pentyl, neopentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl and n-docosyl, preferably $C_1$-$C_{22}$-alkyl such as methyl, ethyl, n-propyl, isopropyl, n-butyl, sec-butyl, isobutyl, tert-butyl, n-pentyl, isopentyl, sec-pentyl, tert-pentyl, neopentyl, n-hexyl, n-heptyl, n-octyl, n-nonyl, n-decyl, n-undecyl, n-dodecyl and stearyl, particularly preferably $C_1$-$C_4$-alkyl such as methyl, ethyl, n-propyl, isopropyl, n-butyl, isobutyl, sec-butyl, tert-butyl; $C_1$-$C_4$-alkoxy such as methoxy, ethoxy, n-propoxy and n-butoxy, carboxyl, $C_1$-$C_4$-alkoxy-carbonyl such as methoxycarbonyl, ethoxycarbonyl, n-propoxycarbonyl and n-butoxycarbonyl, amino-carbonyl, $C_1$-$C_4$-alkylaminocarbonyl such as methylaminocarbonyl, ethylaminocarbonyl, n-propylaminocarbonyl and n-butylaminocarbonyl, di($C_1$-$C_4$alkyl)aminocarbonyl such as dimethylaminocarbonyl, diethylaminocarbonyl, di(n-propyl)aminocarbonyl and di(n-butyl)aminocarbonyl, nitrilo, nitro, amino, $C_1$-$C_4$-alkylamino such as methylamino, ethylamino, n-propylamino and n-butylamino, di($C_1$-$C_4$-alkyl) amino such as dimethylamino, diethylamino, di(n-propyl) amino and di(n-butyl) amino.

Preferred oxadimethacrylics I are given in Table I.

The compounds of the invention are obtainable in various ways.

The first version on the process for preparing the oxadimethacrylics I starting from a mixture of the acrylics IIa and IIb, $H_2C=C(A)H$ and $H_2C=C(B)H$, comprises first reacting the acrylics II with formaldehyde or formaldehyde donor compounds in the presence of at least one tertiary amine and preferably at least one stabilizer, in particular a polymerization inhibitor. At the same time oxygen or a mixture of oxygen and one more nonreactive gases is passed over or through the reaction mixture. The reaction mixture obtained then essentially contains the two alcohols IIIa and IIIb, $H_2C=C(A)C-H_2OH$ and $H_2C=C(B)CH_2OH$.

The reaction mixture can then be further reacted without isolating the alcohols, or the alcohols can be isolated in a conventional manner and then further reacted. In practice it is more advantageous to carry out the reaction without isolating the alcohols.

The second part of the reaction then comprises heating the reaction mixture containing the alcohols IIIa and IIIb, or the isolated alcohols IIIa and IIIb, in the presence of at least one tertiary amine and of at least one stabilizer while passing oxygen or an oxygen-containing gas mixture (containing further, nonreactive gases) over or through the reaction mixture. This produces a reaction mixture containing the corresponding oxadimethacrylic I, which can be isolated in a conventional manner such as by chromatography, crystallization or extraction.

The acrylics II required for these reactions are either commercially available or obtainable by methods known per se, for example by esterification, transesterification, amidation or aminolysis (see H. Rauch-Puntigam et al., Chemie, Physik und Technologie der Kunststoffe, vol. 9, Springer Verlag, Berlin, 1967), from the corresponding readily available acrylic precursors such as acrylic acid and known derivatives thereof.

The formaldehyde can be used in gas form, and liquid form, for example as an aqueous solution such as formalin or in the form of a solution in an alcohol, or in solid form, for example as paraformaldehyde, trioxane or tetroxocane, or as a hemiacetal.

Furthermore, a tertiary amine or a mixture of different tertiary amines is used, although the use of only one tertiary amine is preferred. Suitable tertiary amines are open-chain aliphatic or cyclic tertiary amines such as trimethylamine, triethylamine, tri-n-propylamine, triisopropylamine, tri-n-butylamine, triisobutylamine, tri-n-pentylamine, methyl-diisopropylamine, N,N-diethylisopropylamine, N,N-dimethylethylamine, N,N-dimethylisopropylamine, tri-2-ethylhexylamine, N-methyldiethylamine, N,N-dimethyl-n-propylamine, N,N-dimethyl-n-butylamine, N,N-dimethyl-isobutylamine, N,N-dimethyl-(2-ethylhexyl)amine, N,N-diisopropyl-(2-ethylhexyl)amine, N,N-di-n-butyl-(2-ethyl-hexyl) amine, N-methyl-di(2-ethylhexyl) amine, N-n-butyl-(2-ethylhexyl)amine, N-isobutyldi(2-ethylhexyl)amine, quinuclidine and 1,4-diazabicyclo[2.2.2]octane (DABCO®), preferably quinuclidine and DABCO®, particularly preferably DABCO®.

The stabilizers used are in general the usual polymerization inhibitors such as hydroquinone, hydroquinone monomethyl ether, p-benzoquinone, phenol, 2,6-dimethylphenol, 2,6-di-tert-butylphenol, methylene blue, diphenylamine, cuptic oleate, ferric acetylacetonate, pyrocatechol, preferably hydroquinone monomethyl ether and hydroquinone monoethyl ether.

The oxygen can be passed in pure form or in the form of a mixture with nonreactive gases, preferably air, over or through the reaction mixture.

In the first stage of the reaction, which results in the formation of the alcohols IIIa and IIIb, the acrylics IIa and IIb and the formaldehyde are in general used in a molar ratio of total acrylic to formaldehyde within the range from 1:1 to 8:1, preferably from 1.0:1 to 2.5:1.

In this reaction the tertiary amine is preferably used in a molar ratio of formaldehyde to amine of from 1:1 to 200:1, preferably from 2:1 to 100:1, particularly preferably from 4:1 to 50:1.

The stabilizer is in general used in amounts of from 10 to 1000 mg per kg of acrylic.

The amount of oxygen used ranges in general from 0.01 to 100, preferably from 0.1 to 20, l/h per kg of acrylic. If air is used as oxygen donor, the gas rate will in general range from 0.01 to 1000, preferably from 1 to 250, l/h per kg of acrylic.

The reaction is in general carried out at from 10° to 100° C., preferably at from 40° to 80° C., particularly preferably at from 60° to 75° C. Furthermore, the reaction is in general carried out under atmospheric pressure. However, it can also be carried out under reduced or superatmospheric pressure, preferably ranging from 80 to 250 kPA. The employment of super-atmospheric pressure is advisable in particular when the reaction is carried out at above 80° C.

Furthermore, the reaction is in general carried out without solvent. However, the reaction can also be carried out in the presence of a suitable solvent such as a $C_5$–$C_8$-alkane, preferably n-pentane, n-hexane, n-heptane, n-octane, isooctane, a carboxylic ester such as ethyl acetate or an aromatic solvent such as benzene, toluene and xylenes, particularly preferably n-hexane, isooctane and toluene, or mixtures thereof.

The reaction time depends chiefly on the reaction temperature, but will in general range from 1 to 6 h.

The resulting alcohols IIIa and IIIb can be isolated by a conventional workup method such as distillation or chromatography.

The second stage of the process of the invention comprises converting the mixture of isolated alcohols IIIa and IIIb obtained in the first stage or the reaction mixture containing these alcohols by heating in the presence of at least one tertiary amine and preferably of at least one stabilizer to form oxadimethacrylic I while at the same time passing oxygen or an oxygen-containing gas mixture comprising further, nonreactive gases over or through the reaction mixture.

The type and amount of amine, stabilizer and solvent correspond to those already discussed in connection with the reaction of the acrylic II to form the alcohols IIIa and IIIb. The oxygen rate will in general be within the range from 0.01 to 1000, preferably from 0.1 to 50, l/h per kg of alcohol compound IIIa and IIIb. If air is used as oxygen donor, the gas rate will in general be within the range from 0.1 to 1000, preferably from 1 to 500, l/h per kg of alcohol compound IIIa and IIIb.

The second stage conversion reaction is in general carried out at from 100° to 200° C., preferably at from 100° to 150° C., and at a pressure which in general will range from 70 to 300 kPa, but which preferably will be atmospheric pressure.

The water of reaction can in general be removed from the reaction mixture by distillation, preferably by rectification.

For this purpose it is a good idea to add an entrainer to the reaction mixture. Suitable entrainers for this purpose are for example aliphatic, cycloaliphatic and aromatic hydrocarbons and carboxylic esters such as n-hexane, n-heptane, isooctane, benzene, toluene, xylene, cyclohexane, ethyl acetate, or the acrylics IIa and IIb if they have not been separated off prior to the reaction. The entrainer will in general be selected to have a boiling point within the range from 80° to 200° C.

The reaction time is dependent on the usual parameters such as temperature, pressure and quantities of the starting materials and will in general range from 4 to 12 h.

It is particularly advantageous that the reaction mixture obtained in the preparation of alcohols IIIa and IIIb from acrylics IIa and IIb by the above-described process can be used for conversion into the oxadimethacrylics I without further workup.

To this end the reaction is advantageously carried out in such a way that first the alcohols IIIa and IIIb are prepared from the acrylics IIa and IIb in the first stage of the above-described process of the invention and then further heating the reaction mixture, without isolating the alcohols IIIa and IIIb, under the conditions described in connection with the preparation of the oxadimethacrylics I (second stage) starting from the alcohols IIIa and IIIb.

The acrylics IIa and IIb still present in the reaction mixture, generally in excess, following the formation of the alcohols IIIa and IIIb by the two-stage process may be separated off prior to the conversion to form the oxadimethacrylic I, for example by distillation. However, this may also be done after the reaction to form the oxadimethacrylic I.

The asymmetrical oxadimethacrylics I of the invention can also be prepared starting from only one acrylic IIa (version B) by proceeding in principle in exactly the same way as in the preparation of the alcohols IIIa and IIIb starting from a mixture of the acrylics IIa and IIb (version A, stage one). Here too, after the acrylic IIa has been reacted with formaldehyde, the resulting alcohol IIIa can be isolated or left in the reaction mixture. However, in contradistinction to the first process the formation of the alcohol IIa is followed by the addition of a further alcohol IIIb, obtained for example by the same method or in some other way, to the isolated alcohol IIIa or the reaction mixture containing the alcohol IIIa. The rest of the process is then carried out analogously to the second stage of the first process (A) by heating the mixture containing the alcohols IIIa and IIIb in the presence of at least one tertiary amine and preferably of at least one stabilizer and at the same time passing oxygen or an oxygen-containing gas mixture comprising further, nonreactive gases over or through the reaction mixture.

The choice of starting materials by type and amount and the process parameters are chosen similarly to the above-described first and second stages of the first process (version A).

It will be readily understood that oxadimethacrylics I can also be prepared directly from the alcohols IIIa and IIIb (version C). This procedure corresponds to the second stage of the first process (A), so that it need not be repeated here.

Type and amount of starting material and the process parameters are chosen similarly to the above-described second stage of the first process (version A).

Here too it is of course also possible to use more than two acrylics of type II or alcohol compounds of type III. In general, however, it is more convenient to start from only pairs of these compounds in order to avoid reaction mixtures containing a plurality of oxadimethacrylics of type I.

Starting from oxadimethacrylics of the general formula I″

$$CH_2=C(E)CH_2-O-CH_2C(COQ)=CH_2 \qquad I''$$

where E is —$COOR^4$ or —$CONR^5R^6$ and Q is —$OR^{10}$ or halogen such as chlorine or bromine with $R^{10}$ having the same meaning as $R^1$, with the proviso that $R^{10} \neq R^7$, it is possible to prepare oxadimethacrylics of the general formula I′

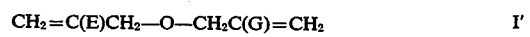
$$CH_2=C(E)CH_2-O-CH_2C(G)=CH_2 \qquad I'$$

where G is —$COOR^7$ or —$CONR^8R^9$ wherein $R^4$ and $R^7$ each have the same meaning as $R^1$, $R^5$ and $R^8$ each have the same meaning as $R^2$, and $R^6$ and $R^9$ each have the same meaning as $R^3$, with the proviso that $R^4 \neq R^7$, $R^5 \neq R^8$ and $R^6 \neq R^9$, by reacting the oxadimethacrylics I″ with an alcohol, $R^7OH$, or an amine, $HNR^8R^9$, in a conventional manner (see Houben-Weyl, Methoden der organischen Chemie, Volume VIII/III, pages 503 ff and pages 647 ff, 1952).

Oxadimethacrylics I″ where Q=—$OR^{10}$ can be obtained by the processes described above. In the case of symmetrical compounds, i.e. in those cases where E=—COOR$^4$ and Q=—OR$^4$, only one acrylic II or alcohol III is used as starting material for the oxadimethacrylics I″ instead of two of these compounds.

Oxadimethacrylics I″ where Q=halogen can be obtained from the corresponding ester compounds (Q=—COOR$^1$) by first hydrolyzing the ester group to obtain the carboxylic acid group and then reacting the carboxylic acid group to form the carbonyl halide, preferably carbonyl chloride, in the conventional manner (see Rauch-Puntigam et al., Chemie, Physik und Technologie der Kunststoffe, Volume 9, page 79, Springer Verlag, Berlin, 1967).

The oxadimethacrylics I prepared by these processes can be isolated by the conventional workup methods such as distillation, crystallization or chromatography.

The oxadimethacrylics I can be used as monomers, comonomers or crosslinkers, in which case the polymerization can be carried out for example by the method described in U.S. Pat. No. 4,889,948. Furthermore, they can be subjected to a 1,6-intra-intermolecular cyclopolymerization to form cyclic ethers by the methods described for example in Polymer Preprints, 31 (1990), 503. This results in a high heat distortion resistance compared with poly(meth)acrylates.

One advantage over symmetrical oxadimethacrylics (A=B) is that by choosing different radicals A and B it is possible to select specifically for certain polymer properties without sacrificing the heat distortion resistance. For instance, the refractive index of an oxadimethacrylic polymer can be raised without sacrificing the good weathering resistance by choosing for the radical A=—COOR$^1$ a short-chain alkyl group such as methyl for R$^1$ while the R$^1$ in the radical B=—COOR$^1$ is made an aromatic radical such as phenyl. Of course, for further optimization it is also possible to prepare copolymers.

For use as coating material or for blending with other polymers such as polyamides it is preferable to use those oxadimethacrylics I in which A is an ester group and B an amide or carboxyl group.

To prepare water-soluble polymers it is possible to use oxadimethacrylics I having a carboxyl group (A) and a carboxamide group (B).

Improved substrate adhesion and adhesivity can be obtained with those oxadimethacrylics I in which at least one group (A and/or B) is a quaternized aminoalkyl ester radical.

EXAMPLES

Example 1

Preparation of Ethyl Methyl 2,2′-[Oxybis(Methylene)]Dipropenoate

A mixture of 430 g (5 mol) of methyl acrylate, 500 g (5 tool) of ethyl acrylate, 135 g (4.5 mol) of paraformaldehyde, 56 g (0.5 mol) of DABCO ® (1,4-diazabicyclo[2.2.2]octane) and 200 g of hydroquinone monomethyl ether was heated at 75° C. for 3 h while at the same time air was passed through the mixture at a rate of 10 l/h. Then with continued heating excess methyl acrylate and ethyl acrylate were distilled off to such an extent that the temperature of the reaction mixture at the base of the column was 140° C. Then the water of reaction was distilled off at 140° C. in the course of 8 h using isooctane as azeotropic entrainer. Thereafter preparative column chromatography of the distillation residue over silica gel using 20/80 ethyl acetate/hexane as mobile phase yielded 39 g of dimethyl 2,2′-[oxybis(methylene)]dipropenoate, 77 g (15.0 %) of ethyl methyl 2,2′-[oxybis(methylene)]dipropenoate, and 53 g of diethyl 2,2′-[oxybis(methylene)]dipropenoate.

Example 2

Preparation of Cyclohexyl Isopropyl 2,2′-[Oxybis(Methylene)]Dipropenoate

A mixture of 308 g (2 mol) of cyclohexyl acrylate, 228 g (2 mol) of isopropyl acrylate, 60 g (2 mol) of paraformaldehyde, 22.4 g (0.2 mol) of DABCO ® and 100 mg of hydroquinone monomethyl ether was heated at 75° C. for 6 h while at the same time air was passed through the mixture at a rate of 10 l/h. Then with continued heating excess cyclohexyl acrylate and isopropyl acrylate were distilled off to such an extent that the temperature of the reaction mixture at the base of the column rose to 125° C. in the course of 14 h. Thereafter preparative column chromatography of the distillation residue over silica gel using 20/80 ethyl acetate/hexane as mobile phase yielded 51 g of isopropyl 2,2′-[oxybis(methylene)bis-2-dipropenoate, 68 g (11.0 %) of cyclohexyl isopropyl 2,2′-[oxybis(methylene)]dipropenoate, and 86 g of cyclohexyl 2,2′-[oxybis(methylene)]dipropenoate.

The products were characterized by elemental analysis and $^{13}$C- and $^1$H-NMR spectroscopy (see Table 1).

TABLE 1

Characterization of products according to the invention $$CH_2=\underset{COOT}{C}-CH_2-O-CH_2\underset{COOT}{C}=CH_2$$

| | Radicals | Yield | Elemental analysis | | | | $^{13}$C (ppm) | NMR $^1$H (ppm) | |
| --- | --- | --- | --- | --- | --- | --- | --- | --- | --- |
| | | | calc. | | found | | | | |
| Ex. | T, T′ | (%) | C | H | C | H | CH$_2$—O | CH$_2$—O | others |
| 1 | Me, Et | 15 | 57.9 | 7.1 | 57.7 | 7.1 | 68.9 | 4.20 | COCH$_3$ = 3.7 COCH$_2$ = 4.1 —CH$_3$ = 1.3 |
| 2 | i-Pr, cy-Hex | 11 | 65.8 | 8.4 | 65.4 | 8.5 | 68.8 | 4.25 | |

We claim:

1. A process for preparing oxadimethacrylics of the formula $$CH_2=C(A)CH_2-O-CH_2C(B)=CH_2 \qquad I$$

where A and B are selected from the group consisting of $-COOR^1$, $-COR^1$, $-CONR^2R^3$ and $-CN$ with the proviso that $A \neq B$ and is not $-COOH$, and $R^1$, $R^2$ and $R^3$ are each defined as follows:

$R^1$ is hydrogen, $C_1$-$C_8$-alkyl, $C_3$-$C_8$-cycloalkyl, $C_3$-$C_8$-cycloalkyl-$C_1$-$C_5$-alkyl, wherein the cycloalkyl rings may be $C_1$-$C_4$-alkyl- or $C_1$-$C_4$-alkoxy-monosubstituted, -disubstituted or -trisubstituted, hydroxy-$C_1$-$C_5$-alkyl, amino-$C_1$-$C_5$-alkyl, N-$C_1$-$C_4$-alkylamino-$C_1$-$C_5$-alkyl, N,N-di-($C_1$-$C_4$-alkyl)amino-$C_1$-$C_5$-alkyl, $C_6$-$C_{18}$-aryl, $C_6$-$C_{18}$-aryl-$C_1$-$C_4$-alkyl, wherein the aryl groups may carry up to three of the following groups: halogen, $C_1$-$C_{22}$-alkyl, $C_1$-$C_4$-alkoxy, carboxyl, $C_1$-$C_4$-alkoxycarbonyl, aminocarbonyl, $C_1$-$C_4$-alkylaminocarbonyl, di($C_1$-$C_4$-alkyl)aminocarbonyl, nitrilo, nitro, amino, $C_1$-$C_4$-alkylamino, di($C_1$-$C_4$-alkyl)amino;

$R^2$ and $R^3$ are each hydrogen, $C_1$-$C_{18}$-alkyl, $C_3$-$C_8$-cycloalkyl, $C_3$-$C_8$-cycloalkyl-$C_1$-$C_5$-alkyl, wherein the cycloalkyl rings may be $C_1$-$C_4$-alkyl- or $C_1$-$C_4$-alkoxy-monosubstituted, -disubstituted or -trisubstituted, $C_6$-$C_{18}$-aryl, $C_6$-$C_{18}$-aryl-$C_1$-$C_4$-alkyl, wherein the aryl groups may carry up to three of the following groups: halogen, $C_1$-$C_{22}$-alkyl, $C_1$-$C_4$-alkoxy, carboxyl, $C_1$-$C_4$-alkoxycarbonyl, aminocarbonyl, $C_1$-$C_4$-alkylaminocarbonyl, di($C_1$-$C_4$-alkyl)aminocarbonyl, nitrilo, nitro, amino, $C_1$-$C_4$-alkylamino, di($C_3$-$C_4$-alkyl)amino;

which process comprises:
reacting a mixture of two different acrylics of the formula IIa and IIb $$H_2C=C(A)H \qquad IIa$$
$$H_2C=C(B)H \qquad IIb$$

with formaldehyde or a formaldehyde donor compound in the presence of oxygen and at least one tertiary amine to form an alcohol of the formulae $$H_2C=C(A)CH_2OH \qquad IIIa$$
$$H_2C=C(B)CH_2OH \qquad IIIb$$

and then converting either the reaction mixture containing these alcohols, or the isolated alcohols IIIa and IIIb, into the corresponding oxadimethacrylic I by heating in the presence of oxygen and at least one tertiary amine.

2. A process for preparing oxadimethacrylics of the formula I'

$$CH_2=C(E)CH_2-O-CH_2C(G)=CH_2 \qquad I'$$

where E is $-COOR^4$ or $-CONHR^5R^6$ and G is $-COOR^7$ or $-CONR^8R^9$ wherein $R^4$ and $R^7$ each have the same meaning as $R^1$, $R^5$ and $R^8$ each have the same meaning as $R^2$ and $R^6$ and $R^9$ each have the same meaning as $R^3$, and $R^1$, $R^2$ and $R^3$ are each defined as follows:

$R^1$ is hydrogen, $C_1$-$C_{18}$-alkyl, $C_1$-$C_8$-cycloalkyl, $C_3$-$C_8$-cycloalkyl-$C_3$-$C_5$-alkyl, wherein the cycloalkyl rings may be $C_1$-$C_4$-alkyl- or $C_1$-$C_4$-alkoxy-monosubstituted, -disubstituted or -trisubstituted, hydroxy-$C_1$-$C_5$-alkyl, amino-$C_1$-$C_5$-alkyl, N-$C_1$-$C_4$-alkylamino-$C_1$-$C_5$-alkyl, N,N-di-($C_1$-$C_4$-alkyl)amino-$C_1$-$C_5$-alkyl, $C_6$-$C_{18}$-aryl, $C_6$-$C_{18}$-aryl-$C_1$-$C_4$-alkyl, wherein the aryl groups may carry up to three of the following groups: halogen, $C_1$-$C_{22}$-alkyl, $C_1$-$C_4$-alkoxy, carboxyl, $C_1$-$C_4$-alkoxycarbonyl, aminocarbonyl, $C_1$-$C_4$-alkylaminocarbonyl, di($C_1$-$C_4$-alkyl)aminocarbonyl, nitrilo, nitro, amino, $C_1$-$C_4$-alkylamino, di($C_1$-$C_4$-alkyl)amino;

$R^2$ and $R^3$ are each hydrogen, $C_1$-$C_{18}$-alkyl, $C_3$-$C_8$-cycloalkyl, $C_3$-$C_8$-cycloalkyl-$C_1$-$C_5$-alkyl, wherein the cycloalkyl rings may be $C_1$-$C_4$-alkyl- or $C_1$-$C_4$-alkoxy-monosubstituted, -disubstituted or -trisubstituted, $C_4$-$C_{18}$-aryl, $C_4$-$C_{18}$-aryl-$C_1$-$C_4$-alkyl, wherein the aryl groups may carry up to three of the following groups: halogen, $C_1$-$C_{22}$-alkyl, $C_1$-$C_4$-alkoxy, carboxyl, $C_1$-$C_4$-alkoxycarbonyl, aminocarbonyl, $C_1$-$C_4$-alkylaminocarbonyl, di($C_1$-$C_4$-alkyl)aminocarbonyl, nitrilo, nitro, amino, $C_1$-$C_4$-alkylamino, di($C_1$-$C_4$-alkyl)amino;

with the proviso that $R^4 \neq R^7$, $R^5 \neq R^8$ and $R^6 \neq R^9$ which comprises reacting oxadimethacrylics of the formula I''

$$CH_2=C(E)CH_2-O-CH_2C(COQ)=CH_2 \qquad I''$$

where Q is $-OR^{10}$ or halogen, wherein $R^{10}$ has the same meaning as $R^1$, with the proviso that $R^{10} \neq R^7$, with an alcohol, $R^7OH$, or an amine, $HNR^8R^9$.

3. A process according to claim 1 for preparing oxadimethacrylics of the formula I $$CH_2=C(A)CH_2-O-CH_2C(B)=CH_2 \qquad I$$

where A and B are selected from the group consisting of $-COOR^1$, $-COR^1$, $-CONR^2R^3$ and $-CN$ with the proviso that $A \neq B$ and is not $-COOH$, wherein $R^1$, $R^2$ and $R^3$ are each defined as follows:

$R^1$ is hydrogen, $C_1$-$C_{18}$-alkyl, $C_3$-$C_8$-cycloalkyl, $C_3$-$C_8$-cycloalkyl-$C_1$-$C_5$-alkyl, wherein the cycloalkyl rings may be $C_1$-$C_4$-alkyl- or $C_1$-$C_4$-alkoxy-monosubstituted, -disubstituted or -trisubstituted, hydroxy-$C_1$-$C_5$-alkyl, amino-$C_1$-$C_5$-alkyl, N-$C_1$-$C_4$-alkylamino-$C_1$-$C_5$-alkyl, N,N-di-($C_1$-$C_4$-alkyl)amino-$C_1$-$C_5$-alkyl, $C_6$-$C_{18}$-aryl, $C_6$-$C_{18}$-aryl-$C_1$-$C_4$-alkyl, wherein the aryl groups may carry up to three of the following groups: halogen, $C_1$-$C_{22}$-alkyl, $C_1$-$C_4$-alkoxy, carboxyl, $C_1$-$C_4$-alkoxycarbonyl, aminocarbonyl, $C_1$-$C_4$-alkylaminocarbonyl, di($C_1$-$C_4$-alkyl)aminocarbonyl, nitrilo, nitro, amino, $C_1$-$C_4$-alkylamino, di($C_1$-$C_4$-alkyl)amino;

$R^2$ and $R^3$ are each hydrogen, $C_1$-$C_{18}$-alkyl, $C_1$-$C_8$-cycloalkyl, $C_3$-$C_8$-cycloalkyl-$C_1$-$C_5$-alkyl, wherein the cycloalkyl rings may be $C_1$-$C_4$-alkyl- or $C_1$-$C_4$-alkoxy-monosubstituted, -disubstituted or -trisubstituted, $C_6$-$C_{18}$-aryl, $C_6$-$C_{18}$-aryl-$C_1$-$C_4$-alkyl, wherein the aryl groups may carry up to three of the following groups: halogen, $C_1$-$C_{22}$-alkyl, $C_1$-$C_4$-alkoxy, carboxyl, $C_1$-$C_4$-alkoxycarbonyl, aminocarbonyl, $C_1$-$C_4$-alkylaminocarbonyl, di($C_1$-$C_4$-alkyl)aminocarbonyl, nitrilo, nitro, amino, $C_1$-$C_4$-alkylamino, di($C_1$-$C_4$-alkyl)amino;

which process comprises reacting an acrylic IIa with formaldehyde or a formaldehyde donor compound in the presence of oxygen and of at least one tertiary amine to form the alcohol IIIa and then reacting the isolated alcohol IIIa or the reaction mixture containing the nonisolated alcohol IIIa with a further, different alcohol IIb by heating in the presence of oxygen and of at least one tertiary amine to form the oxadimethyacrylic.

4. A process according to claim 1 for preparing oxadimethacrylics of the formula I $$CH_2C(A)CH_2-O-CH_2C(B)=CH_2 \qquad I$$

where A and B are selected from the group consisting of $-COOR^1$, $-COR^1$, $-CONR^2R^3$ and $-CN$ with the proviso that A≠B and is not $-COOH$, which comprises converting a mixture of two different alcohols IIIa and IIIb into the oxadimethacrylic I by heating in the presence of oxygen and of at least one tertiary amine.

* * * * *

UNITED STATES PATENT AND TRADEMARK OFFICE
CERTIFICATE OF CORRECTION

PATENT NO.: 5,354,895                                   Page 1 of 2

DATED:      October 11, 1994

INVENTOR(S): BESECKE et al.

It is certified that error appears in the above-identified patent and that said Letters Patent is hereby corrected as shown below:

<u>IN THE ABSTRACT</u> : Title page, item [57], col. 2,

Line 1: "pollers" should read -- polymers --

Line 25: "$C_8$", both occurences, should read -- $C_6$ --

Claim 1, column 9, line 10:
   "$C_1$-$C_8$-alkyl" should read -- $C_1$-$C_{18}$-alkyl --

Claim 1, column 9, line 34:
   "$C_3$" should read --$C_1$--

Claim 2, column 9, line 60:
   "$CONHR^5R^{6'}$" should read -- $CONR^5R^6$ --

Claim 2, column 9, line 66:
   "$C_1$", second occurrence, should read -- $C_3$ --

Claim 2, column 9, line 67:
   "$C_3$", second occurrence, should read --$C_1$--

Claim 2, column 10, line 16:
   "$C_4$", both occurrences, should read -- $C_6$ -- . (1st and 2nd occurrences)

UNITED STATES PATENT AND TRADEMARK OFFICE
CERTIFICATE OF CORRECTION

PATENT NO. : 5,354,895
DATED : October 11, 1994
INVENTOR(S) : Besecke, et. al.

It is certified that error appears in the above-indentified patent and that said Letters Patent is hereby corrected as shown below:

Claim 3, column 10, line 57:
"$C_1$", second occurrence, should read -- $C_3$ --

Claim 3, column 11, line 7:
"IIb" should read -- IIIb --

Claim 3, column 11, line 8:
"oxadimethya-" should read -- oxadimetha- --

Signed and Sealed this

Thirteenth Day of December, 1994

Attest:

BRUCE LEHMAN

Attesting Officer         Commissioner of Patents and Trademarks